US011696794B2

(12) United States Patent
Walberg et al.

(10) Patent No.: US 11,696,794 B2
(45) Date of Patent: Jul. 11, 2023

(54) METHOD AND DEVICE FOR CONTROLLING THE ENERGY SUPPLY TO A MEDICAL INSTRUMENT

(71) Applicant: Aesculap AG, Tuttlingen (DE)

(72) Inventors: Erik Walberg, Tuttlingen (DE); Stefan Eick, Tuttlingen (DE); Anton Keller, Dürbheim (DE)

(73) Assignee: Aesculap AG, Tuttlingen (DE)

(*) Notice: Subject to any disclaimer, the term of this patent is extended or adjusted under 35 U.S.C. 154(b) by 958 days.

(21) Appl. No.: 16/322,666

(22) PCT Filed: Jul. 31, 2017

(86) PCT No.: PCT/EP2017/069296
§ 371 (c)(1),
(2) Date: Feb. 1, 2019

(87) PCT Pub. No.: WO2018/024665
PCT Pub. Date: Feb. 8, 2018

(65) Prior Publication Data
US 2019/0159824 A1 May 30, 2019

(30) Foreign Application Priority Data
Aug. 5, 2016 (DE) .......................... 102016114537.8

(51) Int. Cl.
*A61B 18/12* (2006.01)
*A61B 34/00* (2016.01)
(Continued)

(52) U.S. Cl.
CPC .......... *A61B 18/1206* (2013.01); *A61B 34/25* (2016.02); *A61B 18/1445* (2013.01);
(Continued)

(58) Field of Classification Search
CPC ............ A61B 2018/00916; A61B 2018/00958
See application file for complete search history.

(56) References Cited

U.S. PATENT DOCUMENTS 5,720,742 A * 2/1998 Zacharias .............. A61B 17/29
606/1
10,064,675 B2 9/2018 Rencher et al.
(Continued)

FOREIGN PATENT DOCUMENTS

| CN | 103519883 A | 1/2014 |
| CN | 104042324 B | 9/2014 |

(Continued)

OTHER PUBLICATIONS

German Search Report for German Application No. 10 2016 114 537.8, dated Mar. 27, 2017, with English translation—16 pages.
(Continued)

*Primary Examiner* — Joanne M Rodden
*Assistant Examiner* — Sean W Collins
(74) *Attorney, Agent, or Firm* — Christopher A. Rothe; Culhane Meadows, PLLC

(57) ABSTRACT

A device for controlling the energy supply to a medical instrument contains the medical instrument and an energy supply device. The energy supply device has at least a first and a second energy supply mode that can be preselected on the energy supply device and which supplies energy to the medical instrument according to a preselected energy supply mode. The energy supply device additionally has a third mode which differs from the at least two energy supply modes, can be preselected on the energy supply device, can detect an actuation of an energy supply operating element arranged on the medical instrument, and can carry out the supply of energy to the medical instrument in the first or second mode based on the detected actuation.

13 Claims, 2 Drawing Sheets

Figure 1:
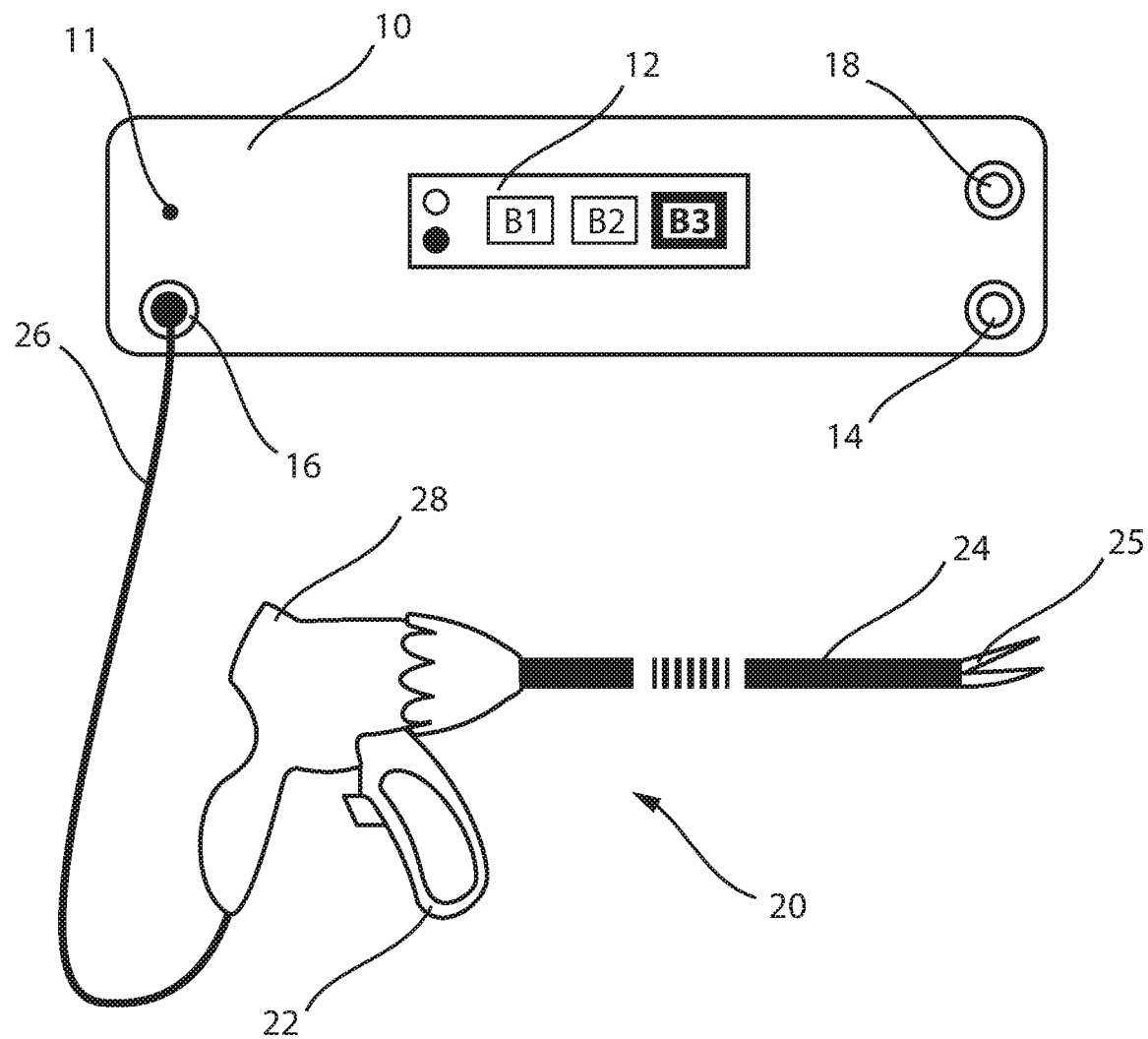

(51) Int. Cl.
    *A61B 18/00* (2006.01)
    *A61B 18/14* (2006.01)
    *A61B 17/00* (2006.01)

(52) U.S. Cl.
    CPC ............ *A61B 2017/00199* (2013.01); *A61B 2017/00367* (2013.01); *A61B 2018/0063* (2013.01); *A61B 2018/00404* (2013.01); *A61B 2018/00702* (2013.01); *A61B 2018/00886* (2013.01); *A61B 2018/00916* (2013.01); *A61B 2018/00928* (2013.01); *A61B 2018/00958* (2013.01); *A61B 2018/126* (2013.01)

(56) References Cited

U.S. PATENT DOCUMENTS

| | | |
|---|---|---|
| 2003/0176778 A1 | 9/2003 | Messing et al. |
| 2006/0217700 A1* | 9/2006 | Garito .................... A61B 18/12 606/34 |
| 2009/0062786 A1 | 3/2009 | Garito et al. |
| 2011/0319882 A1* | 12/2011 | Kennedy ............ A61B 18/1206 606/33 |
| 2015/0335374 A1 | 11/2015 | Konesky et al. |
| 2016/0174819 A1 | 6/2016 | Ouyang et al. |
| 2017/0215945 A1* | 8/2017 | Teigan ............... A61B 18/1447 |
| 2017/0245923 A1* | 8/2017 | Takashino ........... A61B 18/085 |

FOREIGN PATENT DOCUMENTS

| | | |
|---|---|---|
| DE | 19943792 A1 | 4/2001 |
| DE | 102008018406 B3 | 7/2009 |
| EP | 2792326 A1 | 10/2014 |

OTHER PUBLICATIONS

International Search Report and Written Opinion for Application No. PCT/EP2017/069296, dated Oct. 24, 2017—9 pages.
Office Action received in Chinese Application No. 201780048360.0 dated May 6, 2021, with translation, 12 pages.
Search Report received in Chinese Application No. 201780048360.0 dated Apr. 21, 2021, with translation, 5 pages.

* cited by examiner

METHOD AND DEVICE FOR CONTROLLING THE ENERGY SUPPLY TO A MEDICAL INSTRUMENT

RELATED APPLICATIONS

This application is the United States national phase entry of International Application No. PCT/EP2017/069296, filed Jul. 31, 2017, which claims the benefit of priority of German Application No. 10 2016 114 537.8, filed Aug. 5, 2016. The contents of International Application No. PCT/EP2017/069296 and German Application No. 10 2016 114 537.8 are incorporated by reference herein in their entireties.

FIELD

The invention relates to a method and a device for controlling an energy supply to a medical instrument, and refers in particular to a method and a device for selecting one of the modes of an energy supply device of a medical instrument in a medical apparatus or system for bipolar vessel sealing.

BACKGROUND

In open and laparoscopic surgery, for example, apparatus or systems for bipolar vessel sealing are known for instance in the surgical disciplines of general surgery, gynecology, urology and thoracic surgery.

Such known apparatus and systems may include bipolar vessel sealing instruments, which have one distal end provided with a cutting and sealing section by means of which a surgeon can make cuts in tissue parts and vessels and then close or seal cut areas and/or vessels, and comprise a high-frequency (HF) generator to supply energy to the instruments.

So far, a basic setting, such as a mode selection, can be made independently of a connected instrument on the high-frequency generator, and the energy supply to the instrument can then be started and ended via operating elements located on the instrument, such as switches or buttons. In practice, for example, a surgeon selects one of possible modes on the high-frequency generator before starting a surgery, and then the high-frequency generator delivers energy corresponding to the selected mode to the sealing section of the instrument connected to the high-frequency generator, after and as long as the surgeon actuates associated operating elements on the instrument.

In a known embodiment, a known radio frequency generator may have two selectable sealing process modes, for instance, more specifically a first, normal or standard mode, which may be a sealing mode with a shorter sealing time, and a second mode, referred to as a plus mode, which may be a sealing mode with a longer sealing time. Furthermore, a handpiece may have an operating element, for example a push button, which controls the start and end of the energy supply.

A disadvantage here is that the operating element only triggers or initiates and/or stops the energy supply mode selected at the generator, i.e. the first or second mode.

Therefore, all known instruments require that an energy supply switch be kept pressed for the duration of the sealing process. If the energy switch is released during the sealing process, the sealing process is interrupted or stopped. In addition, for all instruments known so far, only one energy supply mode is available for an operating element on the instrument or handpiece, since the default setting or presetting must be made on the line-connected high-frequency generator and/or can only be changed there.

To avoid these disadvantages, prior art technology can either provide an additional dedicated operating element (switch) on the instrument, which can be used to change the mode of the high-frequency generator. However, this possibility is purchased by an increased number of dedicated operating elements on the instrument, which can distract the attention of an operating surgeon, impair the operability of the devices and increase the risk of operating errors during ongoing treatment.

SUMMARY

The invention is therefore based on the object of providing a method and a device for controlling the energy supply to a medical instrument that allow improved user-side control of its energy supply using the components already present on the instrument.

In addition, the user of the medical instrument should be able to select one of the energy supply modes of the medical instrument on the handpiece without additional operating elements on the handpiece.

The invention is based on the general idea of providing a generator mode on an energy supply device for a medical instrument, such as a high-frequency generator supplying a handpiece as the medical instrument or comprising the medical instrument, which generator mode detects a pressing and/or holding period of an operating element on the handpiece and, based on the detected period, makes changes to parameters or parameter settings of the energy supply to the handpiece.

This general idea is described in more detail below on the basis of an example of a bipolar vessel sealing device comprising a handpiece and a high-frequency generator supplying the handpiece with high-frequency energy.

A generator mode can be provided on the high-frequency generator which detects the pressing and/or holding time of an energy supply operating element on the handpiece that switches the high-frequency energy on or off, such as a switch or push button, to make changes to sealing parameters (parameters affecting the sealing process at the treatment site) based on the detected time.

Part of the general idea is, on the one hand, to allow control on the instrument or handpiece without any additional push buttons or switches and to use merely those components of the instrument that already exist on the (existing) instrument or handpiece. Part of the above general idea is also that the user can select and/or switch or change a mode without additional hand movements or steps that interrupt the sequence or flow of a procedure, sequence of procedures or course of treatment, and without communication with, for example, clinical staff. Finally, part of the above general idea is also an intuitive solution in such a way that a method or procedure for defining or selecting a mode is similar to a desired result, i.e. a desired result at least implies a corresponding actuation on the handpiece.

For this purpose, for example, a further, e.g. third mode can be preferably added to the modes already existing on the high-frequency generator, which can be selected or preselected on the high-frequency generator and, after selection or preselection, releases or activates an additional functionality of the energy supply operating element already existing on the handpiece, which in this case can work as a kind of "fire button", for example.

If this mode is selected or preselected on the high-frequency generator, the latter can monitor and/or record the length of time during which the energy supply operating element is held down on the handpiece.

If the energy supply operating element is only operated for a predetermined first (short) time or duration, the high-frequency generator will detect this and provide energy according to a (cycle-related short) normal or standard mode (in the exemplary case of a vessel sealing with short sealing time, a first or normal mode, for example). In contrast, if the energy supply operating element is operated for a predetermined second (longer) time or duration, e.g. 0.8 seconds or more (in the order of one second), the energy supply device will detect this longer lasting actuation and supply energy according to a (cycle-related longer) mode (in the exemplary case of a vessel sealing with longer sealing time, a second or "plus" mode, for example).

Alternatively or additionally, this further or third mode, which is selected at the high-frequency generator, can result in a variable change of the sealing parameters. For example, if the energy supply operating element is briefly pressed, a "standard energy supply" may be provided, for example for a "standard sealing" as a basic sealing mode. In addition, the longer the energy supply operating element is pressed, an increasingly stronger change or adaptation of the sealing process parameters can occur.

In accordance with the above general idea, various configurations can be realized regarding how the high-frequency generator performs the energy supply to the handpiece or instrument and when it starts with it.

In an exemplary possible configuration, the high-frequency generator can wait until it is determined which one of the energy delivery cycles or energy delivery cycles is requested via the handpiece and then start the requested cycle.

In an exemplary possible further configuration, the high-frequency generator can immediately start with parameters corresponding to or assigned to a standard mode as soon as the energy supply operating element is actuated (pressed), and then update the process or cycle to changed parameters, for example those of the plus mode as mentioned above, after it has detected or when it detects a corresponding need. In this case, it is assumed that the time required to detect or determine a desired mode is sufficiently short and does not significantly affect the sealing process flow in terms of parameter change. Depending on parameters, the high-frequency generator may be designed to contain and handle process data for several, for example two, sealing processes until a final decision is made about an actual mode to be performed.

In addition, this mode can be designed to have a varying effect on the sealing parameters. For example, the duration during which the energy supply operating element is held (pressed) can be used to have more than two variable effects on the course of the sealing process. In a practical embodiment, when held for only approximately one second (pressed), either a gentle or a gradual increase in sealing parameters may be provided for, and when held (pressed) longer, this effect can be enhanced or accelerated.

Specifically, the object is achieved by an energy supply control device of a medical instrument adapted to operate an energy supply device of the medical instrument in a plurality of different energy supply modes in response to a selection by an operator, the energy supply control device including at least one actuation detection mode adapted to detect one or more characteristics of a manual actuation of an energy supply operating element and/or an instrument operating element arranged on the medical instrument and, on the basis of the detected actuation characteristic(s), to operate the energy supply device in a first mode or a second mode differing therefrom or preferably in a further mode different therefrom.

In other words, the object is achieved by a device for controlling the energy supply to a medical instrument, comprising the medical instrument; and an energy supply device which is provided to supply energy to the medical instrument, the energy supply device having an actuation detection mode which is intended to detect an actuation of an energy supply operating element arranged on the medical instrument and, on the basis of the detected actuation, to carry out the energy supply to the medical instrument in a first mode or a second mode.

Alternatively or additionally, the object is achieved by a device for controlling the energy supply to a medical instrument, containing: the medical instrument; and energy supply device which has at least one first and a second energy supply mode that can be preselected on the energy supply device and which is provided for supplying energy to the medical instrument according to a preselected energy supply mode. The energy supply device has a third mode/actuation detection mode which differs from the at least two energy supply modes, can be preselected on the energy supply device and is provided for detecting an actuation of an energy supply operating element arranged on the medical instrument and for carrying out the supply of energy to the medical instrument in the first or second mode on the basis of the detected actuation.

In practice, the medical instrument may be a bipolar vessel sealing instrument having a tool and a handpiece on which is arranged an operating element for starting and/or stopping the supply of energy to the instrument, and the energy supply device may be a high-frequency generator for outputting high-frequency energy in one of at least two different modes. The first mode may be a default mode with a first high-frequency energy output and the second mode may be a selectable mode with a second energy output higher than the first high-frequency energy output, and the third mode may be a mode which sets or controls the first or second mode according to a time of pressing or holding the operating element measured or counted by a time measuring device or a counter in the energy supply device, according to which the actual high-frequency energy output to the medical instrument is then effected.

Preferably, the energy supply is configured to detect, in the third mode/the actuation detection mode, a period of actuation of the energy supply/instrument operating element as the actuation characteristic and/or an actuating force exerted on the energy supply/instrument operating element, and to provide energy to the medical instrument in the first or second mode depending on the detected period of time. Against the background of an improvement of an existing arrangement to be created, the addition of a third and thus superordinate mode to already existing at least two modes permits a clearly presentable functional extension of the existing arrangement without the need for far-reaching changes or interventions with regard to the already existing functional and/or mechanical configuration.

According to the invention, provision may be made that the first mode and/or the second mode and the third mode/activation detection mode can be manually preselected on the energy supply device in direct fashion, which differ in each case and are intended to supply energy to the medical instrument in accordance with the preselected energy supply mode. For example, if the first mode and the third mode can be preselected, the second mode can only be selected and executed by an appropriate/suitable, preferably long, actuation of the energy supply operating element in the third mode. If only the second mode and the third mode can be preselected, the first mode can only be selected and executed by an appropriate/suitable, preferably short, actuation of the energy supply operating element in the third mode. It should be noted that if only the third mode/the actuation detection mode can be preselected, both the first and second modes can only be selected and executed by appropriate actuation of the energy supply operating element.

Preferably, the first mode is a preset default mode intended to carry out the energy supply of the medical instrument on the basis of first parameter settings, and the second mode is a mode that can be selected via a mode selection device on the energy supply device and has an effect differing from that of the first mode and intended to carry out the energy supply of the medical instrument on the basis of second parameter settings. The term "first and second parameter settings" are to be understood both as the setting of different parameters and the setting of different values for individual parameters. A changed effect of the parameter settings means different manifestations of the sealing (quick sealing/stapling or final quality sealing) and the associated consequences (in terms of sealing performance and the formation of thermal tissue damage). These at least two modes allow a vessel sealing system to carry out, for instance, a short-term sealing process in the first mode and a longer lasting sealing process in the second mode.

The energy supply device is preferably configured, in the third mode, to detect an operating period of the energy supply operating element arranged on the medical instrument and to compare the detected operating period with a predetermined, in particular preset, operating period threshold value in such a way that a supply of energy to the medical instrument is selected and executed in the first mode when the detected operating period is less than the operating period threshold value, and a supply of energy to the medical instrument is selected and executed in the second mode when the detected operating period is greater than or equal to the operating period threshold value. In this manner, it is advantageous to additionally use a fire button—which is already provided on a handpiece of the medical instrument and by means of which the energy supply device is basically controllable for starting an energy output and ending an energy output in the preselected first or second mode—in the preselected third mode to activate the first or second mode on the energy supply device, depending on how long it is pressed or kept pressed.

Preferably, the operating period threshold value is up to one second, preferably between 0.8 seconds and 1.0 seconds, further preferably amounts to exactly 0.8 seconds. It is advantageous if the period of time during which the control button on the medical instrument is to be kept depressed by a user is within time periods that can be easily distinguished by the user for the safe activation of the first or second mode.

If the third mode is preselected on the energy supply device and the energy supply of the medical instrument is performed in at least the second mode, the energy supply is preferably configured to change and/or adjust parameter settings of the energy supply of the medical instrument depending on a detected operating period of the energy supply operating element. If not only the elapse of the first operating period is detected to identify the need to perform the second mode, but also the duration of the subsequent actuation of the operating element, it is advantageous to map and/or apply changes to process parameters that vary depending on the actual duration of the actuation of the operating element, e.g. an increase or decrease.

In the third mode, the energy supply device is preferably intended to determine an energy delivery cycle requested via the energy supply operating element of the medical instrument according to the first or second mode and then to start the requested energy delivery cycle. In such an embodiment, it is advantageous to wait until the time foreseen for the first mode has elapsed and determine whether or not the operating element is kept pressed beyond that and the second mode is requested. In this way, the mode actually desired by the user can be reliably provided.

Alternatively or additionally preferred, the energy supply device may be configured to start a first energy delivery cycle in the first mode as a standard mode after detecting a first actuation of the energy supply operating element and to change to a second energy delivery cycle with parameter settings corresponding to the second mode upon detecting a continued actuation of the energy supply operating element with a duration associated with the second mode. In such an embodiment, it is advantageous not to wait until the time foreseen for the first mode has elapsed, but to wait for a decision on the request of the first or second mode, which could otherwise be made at the earliest after the time foreseen for the first mode has elapsed. In this way, the energy supply can be started immediately in a basic supply mode and the medical instrument can be supplied with energy without delay.

It should be noted that further developments of the two above-mentioned types or alternatives can also be implemented as the third and a further, i.e. fourth mode that can be preselected on the energy supply device, or the third mode can be switched over accordingly via a predetermined sequence of (presetting) actuations of the operating element on the handpiece. For example, a design can be such that a predetermined repeated pressing of the operating element in short succession switches back and forth between an immediate start of the energy supply and a delayed start of the energy supply.

At least when the delayed start of the energy supply is selected, it is preferred to configure the energy supply device to hold and handle process data for the first energy delivery cycle and the second energy delivery cycle in parallel at least until a mode which is actually to be carried out can be determined on the basis of the detected duration. In this way, it is advantageous to support a delay-free determination of the actual mode after the first period of time has elapsed.

The energy supply device is preferably intended to continuously or gradually increase and decrease process parameters in the third mode when performing the first and/or second mode, and to increase or decrease the process parameters more strongly than in the first mode when performing the second mode.

The medical instrument is preferably a bipolar vessel sealing instrument and the energy supply device is a high-frequency generator for supplying the bipolar vessel sealing instrument with high-frequency energy.

A vessel sealing instrument and a high-frequency generator can advantageously form at least part of a bipolar vessel sealing system which includes a device as briefly described above.

In addition, a method for controlling the energy supply from an energy supply device to a medical instrument in at least a first or a second energy supply mode preferably includes the steps of determining whether a third mode is preselected on the energy supply device, and if the third mode is preselected, determining whether an energy supply operating element on the medical instrument is actuated, and if the energy supply operating element is actuated, performing the energy supply to the medical instrument in the first or second mode on the basis of the detected actuation.

It is preferred that the method in the third mode detects a period of time during which the energy supply operating element is actuated and performs the supply of energy to the medical instrument in the first or second mode depending on the detected period of time.

In the method, the first mode may be advantageously a preset default mode intended to carry out the energy supply of the medical instrument on the basis of first parameter settings, and the second mode may be a mode that can be selected via a mode selection device on the energy supply device and has an effect differing from that of the first mode and intended to carry out the energy supply of the medical instrument on the basis of second parameter settings.

The method may preferably be configured to detect, in the third mode, an operating period of the energy supply operating element arranged on the medical instrument and to compare the detected operating period with a predetermined, in particular preset, operating period threshold value in such a way that an energy supply of the medical instrument is selected and executed in the first mode if the detected operating period is less than the operating period threshold value, and an energy supply of the medical instrument is selected and executed in the second mode if the detected operating period is greater than or equal to the operating period threshold value.

It may be advantageous that the operating period threshold value is up to one second, preferably between 0.8 seconds and 1.0 seconds, further preferably exactly 0.8 seconds.

Further, when the third mode is preselected on the energy supply device and the energy supply to the medical instrument is performed in the second mode, preferably the method may, in the third mode, change and/or adjust parameter settings of the energy supply to the medical instrument depending on a detected duration of actuation of the energy supply operating element.

It may also be preferred that the method in the third mode determines an energy delivery cycle according to the first or second mode requested via the energy supply operating element of the medical instrument and then begin the requested energy delivery cycle.

Alternatively or additionally, it may be preferred that after detecting a first actuation of the energy supply operating element, the method begins a first energy delivery cycle in the first mode as a standard mode and, upon detecting a continued actuation of the energy supply operating element with a duration associated with the second mode, change to a second energy delivery cycle with parameters corresponding to the second mode.

Advantageously, the method may be configured to hold and handle process data for the first energy delivery cycle and second energy delivery cycle in parallel at least until an actual mode to be performed can be determined based on the detected duration.

In addition, it is advantageous if the method is able to continuously or gradually increase and decrease process parameters in the third mode when performing the first and/or second mode, and to increase or decrease the process parameters more strongly than in the first mode when performing the second mode.

The above brief description for the purposes of a first overview is in no way restrictive. The invention can be applied in various devices and methods in which available modes on a first apparatus during a running process are to be influenced from a remote operating unit without additional components on the operating unit.

BRIEF DESCRIPTION OF THE DRAWING FIGURES

Figure 2:
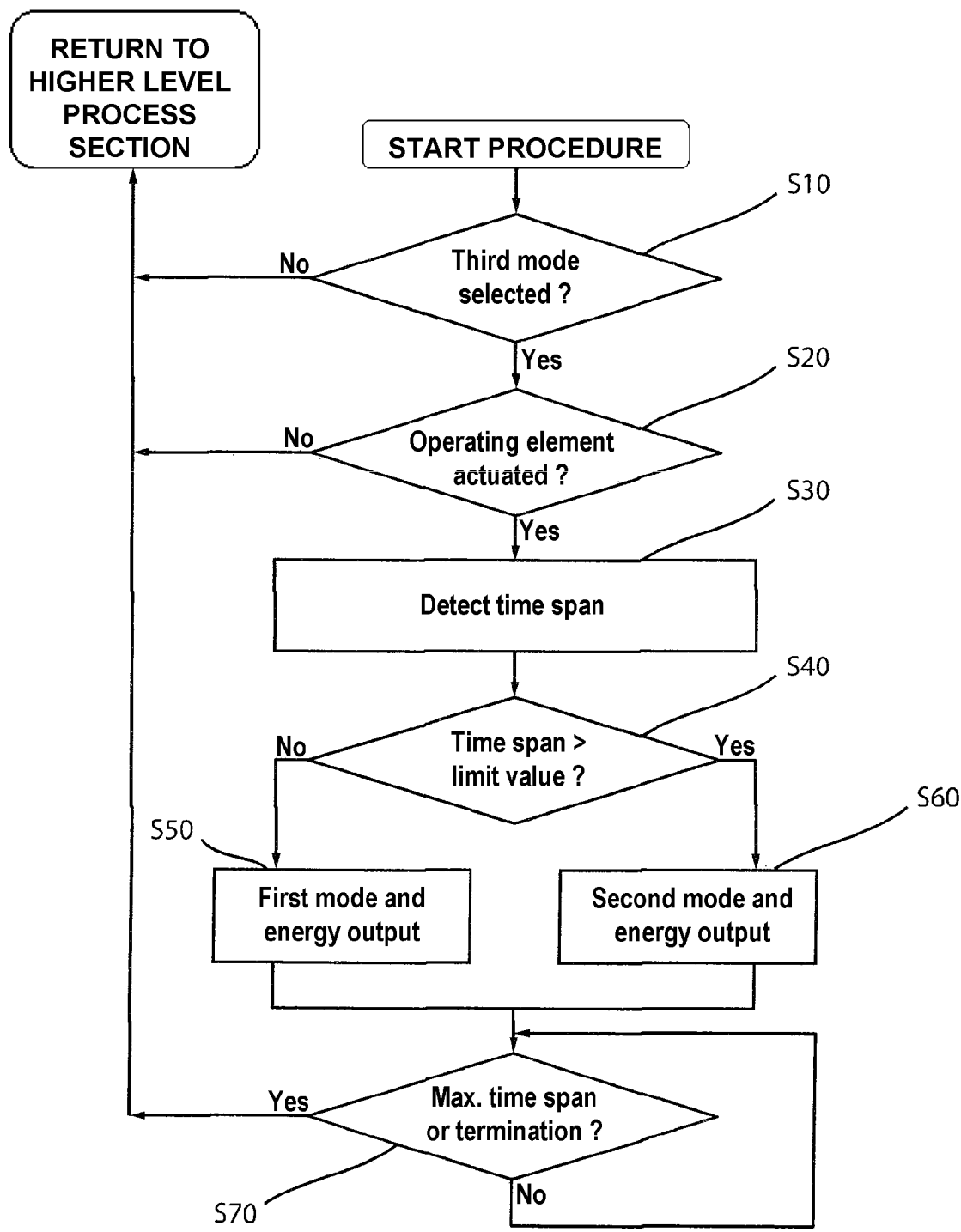

The invention is described in more detail below using a preferred exemplary embodiment with reference to the attached drawing figures. Unless otherwise indicated, the same reference signs in the drawing figures designate identical components that are not described redundantly. In the Figures:

FIG. 1 is a schematic representation of a bipolar vessel sealing system as an exemplary embodiment of a device for controlling the energy supply to a medical instrument; and FIG. 2 shows a flow chart of an exemplary operating procedure in the exemplary embodiment according to FIG. 1.

DETAILED DESCRIPTION

FIG. 1 schematically shows a bipolar vessel sealing system embodying an exemplary embodiment of a device for controlling the energy supply to a medical instrument. It is noted that a basic form of such a bipolar vessel sealing system with two modes as described above is available and known as Aesculap® Caiman® (medical instrument) and Aesculap® Lektrafuse® (high-frequency generator). In this respect, known elements and components are not described redundantly.

According to FIG. 1, the bipolar vessel sealing system thus comprises at least one high-frequency generator 10 and one bipolar vessel sealing instrument 20 electrically connected to the high-frequency generator 10.

The high-frequency generator 10 is arranged in a housing which essentially comprises or houses an electronic system generating high-frequency energy and an electronic processing system including a CPU, associated memory, input/output sections and the like, a mains connection (at the rear; not shown), a mains switch (at the rear; not shown), at least one signaling light 11, a display device 12, a connection for a foot control switch 14, a connection 16 for at least one medical instrument and a mode selector switch 18. The high-frequency generator 10 forms in this embodiment an energy supply device or means for supplying the bipolar vessel sealing instrument 20 with high-frequency energy.

The vessel sealing instrument 20 as a medical instrument comprises a handpiece 22 and a rod- or shaft-shaped tool 24. The tool 24 may have a hinge-type distal end at which a vessel sealing device or vessel sealing section, for instance with two branches 25 pivotable relative to one another and provided with HF electrodes for sealing at least vessels during a surgical intervention and optionally a cutting device or cutting section for making cuts in tissue and/or vessels are arranged. The vessel sealing device compresses the tissue and transfers heat, which is generated from the high-frequency energy or high-frequency supplied to the instrument 20, to the tissue or vessel to be sealed.

The vessel sealing instrument 20 can be connected to the connection 16 of the high-frequency generator 10 by means of a cable 26 and has its handpiece 22 provided with at least one actuating or operating element 28 via which the supply of energy from the high-frequency generator 10 can be requested by actuating or operating it, therefore operating as an energy supply operating element 28. As shown in FIG. 1, the energy supply operating element 28 may be provided as a push button/operating button, but other embodiments are also possible.

In this exemplary embodiment, at least three modes B1, B2, B3 for the sealing process, i.e. a first mode (B1), a second mode (B2) and a third mode (B3), are provided by the high-frequency generator 10 and can be preselected and/or changed on the mode selector switch 18 when the high-frequency generator 10 is switched on.

The high-frequency generator 10 may be configured such that a selected mode is maintained until the high-frequency generator 10 is switched off, can be changed during an intervention, and is independent of a connected instrument. A set mode can be displayed on the display device 12 and marked as selected by means of a frame and/or bold font, for example. In addition, various feedbacks of the high-frequency generator 10 can be provided via light signaling on light sources or display segments of the display device 12 and/or via sound signaling such as beeps. For example, different modes may be distinguished by different flashing frequencies of signaling lights or display segments and/or different frequencies of beeps during a high-frequency output.

A basic operating procedure on the high-frequency generator 10 will be described briefly below. The basic operating procedure includes connecting the high-frequency generator 10 to the electrical mains, switching on the mains switch (an associated signal lamp lights up), performing an automatic self-test, and selecting a desired mode when the automatic self-test is completed and the apparatus is ready. Then, a foot switch, if present, and the bipolar vessel sealing instrument 20 can be connected to the high-frequency generator 10 and activated with the push button or energy supply operating element 28 or the (not shown) foot switch, as appropriate.

In a basic configuration that corresponds to the known arrangement, the sealing process (the HF output) can be started by pressing the energy supply operating element 28 once, for example, and stopped or aborted by pressing it again. Without pressing the energy supply button again, the high-frequency generator 10 will automatically stop the HF output after the sealing process is complete. This means that in the known basic configuration, the mode to be used must be preselected on the high-frequency generator 10 before starting a treatment or a surgery, unless a preset mode is to be retained after switching on the high-frequency generator 10, and the energy supply operating element 28 on the handpiece 22 only triggers the start and, if necessary, the end of an HF output in the mode preselected on the high-frequency generator 10.

According to the present exemplary embodiment, a further, third mode B3 that can be preselected is provided. The third mode B3 is a mode in which the high-frequency generator 10 detects and determines whether and for how long the energy supply operating element 28 on the handpiece 22 is pressed or kept pressed. In accordance with the result of the acquisition or determination of a corresponding duration, the high-frequency generator 10 switches to one of the two HF output modes B1, B2 and/or changes parameters that influence the HF output and may have an effect on the sealing process.

In the following, an operating sequence using the third mode B3 is described in more detail with reference to FIG. 2. A description of the basic operating sequence as mentioned above is not redundantly repeated in FIG. 2. In other words, it is assumed that for the sequence shown in FIG. 2, the high-frequency generator 10 is ready for operation, the vessel sealing element 20 is functionally connected to it and there is a valid presetting or preselection of a mode.

In S10, the high-frequency generator 10 checks whether the third mode B3 is preselected. If the third mode B3 is not preselected (NO in S10), the sequence returns to a higher-level process section, from which it can, for example, cyclically reach S10 again as the entry point into the processing according to FIG. 2. If the third mode B3 is preselected (YES in S10), the processing goes to S20.

In S20, the high-frequency generator 10 checks whether the energy supply operating element 28 on the handpiece 22 is actuated or pressed. If the energy supply operating element 28 is not pressed (NO in S20), the sequence also returns to the higher-level process section. If the energy supply operating element 28 is pressed (YES in S20), the processing goes to S30.

In S30, the high-frequency generator 10 begins to detect a duration or time span during which the energy supply operating element 28 is operated or held down using, for example, a timer or time counter. Processing then proceeds to S40. Before this, the timer can be suitably initialized and/or its last state or counter value can be buffered or stored in a memory of the high-frequency generator 10 for logging purposes, for example.

In S40, the high-frequency generator 10 determines whether the acquired duration is shorter or longer than a predetermined limit value/threshold value. If the detected duration is shorter than the predetermined threshold value, processing goes to S50. If the detected duration is longer than the predetermined limit value, processing goes to S60.

In S50, the high-frequency generator 10—for HF output to the vessel sealing instrument 20—sets the first mode B1 corresponding to a default mode with first parameters for an energy supply in favor of a short sealing process, and outputs the corresponding HF energy to the vessel sealing instrument 20. After the HF energy output to the vessel sealing instrument 20 has begun, processing proceeds to S70.

In S60, the high-frequency generator 10—for HF output to the vessel sealing instrument 20—sets the second mode B2 corresponding to a mode with increased HF output compared to the first mode B1 and with second parameters for an energy supply in favor of a long sealing process, and outputs the corresponding HF energy to the vessel sealing instrument 20. After the HF energy output to the vessel sealing instrument 20 has begun, processing goes to S70.

In S70, the high-frequency generator 10 checks whether a maximum duration of the energy output to the vessel sealing instrument 20 has been reached and/or whether holding down the energy supply operating element 28 on the handpiece 22 is finished. In other words, the high-frequency generator 10 checks whether or not a termination condition has occurred for the current HF output. If it is determined that the termination condition has occurred (YES in S70), the high-frequency generator 10 terminates the time recording and the current energy output, and the processing returns to the higher-level process section, from which S10 can again be reached as entry point into the processing according to FIG. 2. If it is determined that the termination condition did not occur (NO in S70), the query processing according to S70 is repeated.

In a modification of the present exemplary embodiment, a process section with at least one additional step S55 and/or S65 can be provided after, for example, S50 and/or S60, in which parameters (sealing parameters) of the current HF output are updated, changed and/or adapted as a function of a currently recorded time period.

For example, in the third mode B3 provision may be made that in at least one of the modes B1 and B2, preferably the second mode B2, the sealing parameters, starting from suitable initial values, are changed the more strongly, the longer the energy supply operating element 28 is kept pressed, or that the sealing parameters are changed or not changed starting from a predetermined period of pressing, or are changed in increasing or decreasing fashion for a predetermined period of time, or are paused for a change.

If it is planned to change the sealing parameters in several of the modes in a time-dependent manner, the high-frequency generator 10 can maintain or hold process data for the several sealing modes during processing until a final decision has been made on the sealing mode to be defined in accordance with the recorded time, and can carry out a multi-variable influencing, for example a two-fold variable influencing, of the sealing process. If the energy supply operating element 28 is held in this case for about one second, for example, a soft or gradual increase of a change to or on sealing parameters may be made, and if it is held for a longer period of time, this effect or influence may be enhanced, for example accelerated.

In a further modification of the present exemplary embodiment, at least one step S25 can be provided before, for example, S30, in which the HF output is started in the first mode B1 (standard mode) immediately after detection of the actuation of the energy supply operating element 28. In this case, the following step S40 can be used to maintain or change the mode (for example, from mode B1 to mode B2) according to the duration actually recorded in the further course.

In this exemplary embodiment, a generator mode is described as a whole which measures the duration of pressing/holding an operating element or operating key (HF key) in order to effect changes to the sealing parameters, i.e. to control parameter changes with respect to the HF output on the basis of the measured duration.

As described above, a device for controlling the energy supply to a medical instrument includes the medical instrument (vessel sealing instrument 20) and an energy supply device (high-frequency generator 10) having at least a first and a second energy supply mode (modes B1 and B2) that can be preselected on the energy supply device, and is arranged to supply the medical instrument with energy in accordance with a preselected energy supply mode. The device is characterized in that the energy supply device further comprises a third mode (mode B3) that can be preselected on the energy supply device and differs from the at least two energy supply modes and is arranged to detect an actuation of an energy supply operating element (handle or HF button 28) disposed on the medical instrument and to perform the supply of energy to the medical instrument in the first or second mode based on the detected actuation.

The invention has been described above using a preferred exemplary embodiment. It goes without saying that details of the preferred exemplary embodiment described do not restrict the invention as such and may result in various modifications, modifications and/or equivalents for the person skilled in the art, all of which are within the scope of protection of the invention.

The invention claimed is:

1. An energy supply control device adapted to operate an energy supply device of a medical instrument in a plurality of different energy supply modes depending on a selection by an operator, wherein the plurality of different energy supply modes comprise at least a first mode and a second mode different from the first mode, wherein the energy supply control device includes at least an actuation detection mode adapted to detect one or more actuation characteristics of a manual actuation of at least one of an energy supply operating element arranged on the medical instrument or of an instrument operating element and, on the basis of the one or more actuation characteristics, to operate the energy supply device in at least the first mode or the second mode, wherein on the energy supply device, at least one of the first mode, the second mode or the actuation detection mode as a third mode can each be directly preselected manually to supply the medical instrument with energy, and wherein the energy supply device is configured, in the actuation detection mode, to detect said one or more actuation characteristics, said one or more actuation characteristics comprising a pressing or holding time of at least one of the energy supply operating element or of the instrument operating element, the pressing or holding time comprising an actuation time period for which the at least one of the energy supply operating element or the instrument operating element is being pressed by the operator, and to supply energy to the medical instrument in the first mode when the actuation time period for which the at least one of the energy supply operating element or the instrument operating element is being pressed by the operator is less than a predetermined actuation time period threshold value, or to supply energy to the medical instrument in the second mode when the actuation time period for which the at least one of the energy supply operating element or the instrument operating element is being pressed by the operator is greater than or equal to the predetermined actuation time period threshold value.

2. The device according to claim 1, wherein the first mode is a standard preset mode which is provided to supply energy to the medical instrument on the basis of first parameter settings, and the second mode is a mode which can be selected via a mode selection device on the energy supply device and has an effect which differs from that of the first mode and is provided to supply energy to the medical instrument on the basis of second parameter settings.

3. The device according to claim 1, wherein the actuation time period threshold value represents a duration of up to one second.

4. The device according to claim 1, wherein when the third mode is preselected on the energy supply device and the energy supply of the medical instrument is performed in the second mode, the energy supply device is configured to at least one of change or adjust parameter settings of the energy supply of the medical instrument depending on the actuation time period.

5. The device according to claim 1, wherein the energy supply device determines, in the third mode, an energy delivery cycle requested via the energy supply operating element of the medical instrument according to the first or second mode and then starts said energy delivery cycle.

6. The device according to claim 1, wherein the energy supply device is configured to start a first energy delivery cycle in the first mode as a standard mode after detecting a first actuation of the energy supply operating element and to switch to a second energy delivery cycle with parameter settings corresponding to the second mode upon detecting a continued actuation of the energy supply operating element with a duration of the actuation time period associated with the second mode.

7. The device according to claim 6, wherein the energy supply device is configured to hold and to handle process data for the first energy delivery cycle and the second energy delivery cycle in parallel at least until a mode which is actually to be carried out can be determined based on the detected duration of the actuation time period.

8. The device according to claim 1, wherein the energy supply device continuously or in a stepwise manner increases or decreases process parameters in the third mode when at least one of the first mode or the second mode are carried out.

9. The device according to claim 1, wherein the medical instrument is a bipolar vessel sealing instrument and the energy supply device is a high-frequency generator for supplying the bipolar vessel sealing instrument with high-frequency energy.

10. A bipolar vessel sealing system comprising a device according to claim 1.

11. The device according to claim 1, wherein the first mode features a first high-frequency energy output and the second mode features a second high-frequency energy output higher than the first high-frequency energy output.

12. A method for controlling an energy supply from an energy supply device, on which at least one of a first mode, a second mode, or an actuation detection mode as a third mode can each be directly preselected manually, the first mode, the second mode, and the actuation detection mode each being different from each other, to a medical instrument in the actuation detection mode, the method comprising the steps of:

preselecting the actuation detection mode on the energy supply device;

actuating an energy supply operating element on the medical instrument;

detecting one or more actuation characteristics of the energy supply operating element, wherein said one or more actuation characteristics comprises a pressing or holding time of the energy supply operating element, the pressing or holding time comprising an actuation time period for which the energy supply operating element is being pressed by an operator; and supplying energy to the medical instrument in the first mode when the actuation time period for which the energy supply operating element is being pressed by the operator is less than a predetermined actuation time period threshold value, or supplying energy to the medical instrument in the second mode when the actuation time period for which the energy supply operating element is being pressed by the operator is greater than or equal to the predetermined actuation time period threshold value.

13. The method according to claim 12, wherein the first mode features a first high-frequency energy output and the second mode features a second high-frequency energy output higher than the first high-frequency energy output.

* * * * *